(12) United States Patent
Chevalier

(10) Patent No.: US 6,737,067 B1
(45) Date of Patent: May 18, 2004

(54) TRIMER OF HIV ENV GENE EXPRESSION PRODUCT

(75) Inventor: Michel Chevalier, Beaurepaire (FR)

(73) Assignee: Aventis Pasteur S.A., Lyon Cedex (FR)

( * ) Notice: Subject to any disclaimer, the term of this patent is extended or adjusted under 35 U.S.C. 154(b) by 0 days.

(21) Appl. No.: 09/744,659

(22) PCT Filed: Jul. 29, 1999

(86) PCT No.: PCT/FR99/01871

§ 371 (c)(1), (2), (4) Date: Apr. 18, 2001

(87) PCT Pub. No.: WO00/08167

PCT Pub. Date: Feb. 17, 2000

(30) Foreign Application Priority Data

Jul. 31, 1998 (FR) .......................................... 98 10027

(51) Int. Cl.$^7$ .............................................. A61K 39/21
(52) U.S. Cl. ................................ 424/208.1; 424/184.4; 424/186.1; 424/192.1; 530/300; 530/350; 530/402; 530/403
(58) Field of Search ...................... 424/208.1; 530/300, 530/350, 402, 404, 408, 412, 414, 416, 417, 826

(56) References Cited

U.S. PATENT DOCUMENTS 5,122,468 A * 6/1992 Sarngadharan et al. .... 435/70.4
6,140,059 A * 10/2000 Schawaller ............... 424/188.1

FOREIGN PATENT DOCUMENTS

WO  WO9400557  1/1994
WO  WO9916883  4/1999

OTHER PUBLICATIONS

Hallenberger et al. Secreation of a trunctaed form of the HIV type 1 envelope glycoprotein. Virology (1993) vol. 193, pp. 510 514.*
Smyth et al. Reactions of N–ethylmaleimide with peptides and amino acids. Biochemical Journal (1964) vol. 91, pp. 589–595.*
Riordan et al. Reactions with N–ethylmaleimide and p–mercuribenzoate. Methods in Enzymology (1972) vol. 25, pp. 449–445.*
Machuca et al. Human immunodeficiency virus type–2 infection in Spain. Intervirology (1998) vol. 42, pp. 37–42.*
Advanced Bioscience Catalog, Product specification: Viral antigens, pp. 1–3 (2003).*
Rabenstein et al. A peptide from the heptad repeat of human immunodeficiency virus gp41 shows both membrane binding and coiled–coil formation. Biochemistry (1995) vol. 34, No. 41, pp. 13390–13397.*
Lazar et al. Transforming growth factor alpha: mutation of aspartic acid 47 and leucine 48 results in different biological activities. Molecular and Cellular Biology (1988) vol. 8, No. 3, pp. 1247–1252.*
Burgess et al. Possible dissociation of the heparin–binding and mitogenic activities of heparin–binding (acidic fibroblast) growth factor–1 from its receptor–binding activities by site–directed mutagenesis of a single lysine residue. Journal of Cell Biol.*
Bowie et al. Deciphering the message in protein sequences: tolerance to amino acid substitutions. Science (1990) vol. 247, pp. 1306–1310.*
Zaides et al. Extensiv C–terminal deletion in human immunodeficiency virus type 1 Env glycoprotein arising after long–term culture of chronically infected cells. Journal of General Virology (1994) vol. 75, pp. 2963–2975.*
Fahey et al., Statur of immune based therapies in HIV infection and AIDS. Clinical Experimental Immunology (1992) vol. 88, pp. 1–5.*
Letvin, Progress in the development of an HIV vaccine. Science (1998) vol. 280, pp. 1875–1879.*
Wyatt R., et al. "The antigenic structure of the HIV gp120 envelope glycoprotein." Nature. vol. 393, No. 6686, Jun. 18, 1998, pp. 705–711.
Moore and Binley. "Envelope's letters boxed into shape." Nature. vol. 393, No. 6686, Jun. 18, 1998, pp. 630–631.
Lu M. et al. "A trimeric structural domain of the HIV–1 transmembrane glycoprotein." Nature Structured Biology. 2(12), Dec. 1995, pp. 1075–1082.

* cited by examiner

Primary Examiner—Ulrike Winkler
(74) Attorney, Agent, or Firm—McDonnell Boehnen; Hulbert & Berghoff LLP

(57) ABSTRACT

The invention concerns a purified recombinant glycoprotein having the following properties: a) an adherence capacity to CD4; b) an affinity with a anti-gp120 antibody capable of neutralizing in vitro HIV cell infection; c) an affinity with an anti-gp41 antibody; d) a timeric form free from inter-chain disulphide bonds. The invention also concerns a vaccine comprising said purified glycoprotein and an adjuvant. The invention further concerns a method for obtaining said glycoprotein, which consists in expressing, by means of genetic recombining techniques, a glycoprotein corresponding to the properties a), b) and c) mentioned above; purifying it, and subjecting it to steps involving at least a reducing agent, an ionic detergent and/or a neutral detergent in conditions leading to a glycoprotein having said properties.

21 Claims, 1 Drawing Sheet

TRIMER OF HIV ENV GENE EXPRESSION PRODUCT

This application is a 35 U.S.C. § 371 filing of international application PCT/FR99/01871, file Jul. 29, 1999.

The present invention relates to a method for obtaining recombinant proteins, the origin of which is the membrane of the HIV virus responsible for the acquired immunodeficiency syndrome (AIDS), allowing the restoration of their native trimeric form, and to the use of these proteins for the purpose of vaccination or of diagnosis.

STATE OF THE ART

The HIV envelope glycoprotein is encoded by the "env" gene, and the translation of the corresponding mRNA gives a glycosylated protein, gp160, in the form of a precursor with a molecular mass of 160 kDa. gp160 is cleaved inside the cell to give, at the cytoplasmic membrane during budding of the virus in the process of formation, on the one hand gp120, which is found on the outside of the cell and of the virus, and on the other hand gp41, which is the transmembrane portion of the glycoprotein and which corresponds to the carboxy-terminal end of the precursor. Once the viral particle has been released, gp41, the only transmembrane protein, will have its carboxy-terminal end turned toward the inside of the virus and its amino-terminal end projecting on the outside, maintaining itself associated noncovalently with gp120. It is attached noncovalently to gp41 via its amino-terminal end, while the rest of the protein is involved in the recognition of the CD4 receptor and of the CCR5 or CXCR4 coreceptors (specific for auxiliary T4 lymphocytes, macrophages; Trkola et al., J. Virol., 72, 1876–85, 1998; Schols et al., J. Virol., 72, 4032–4037, 1998; Rubbert et al., J. Immunology, 160, 3933–3941, 1998) The binding of gp120 to CD4 makes it possible to expose the membrane of the target cell to the amino-terminal hydrophobic portion of gp41, thereby inducing the mechanism of fusion of the viral and cell membranes, this fusion being the cause of the penetration of the virion into the target cell during infection (Wong-Staal et al., In Molecular Genetic Medecine, 2, Friedman ed., 189–219, 1992; Berger et al., Nature, 391: 240, 1998).

This process of recognition of the viral receptor, followed by the fusion of the membranes due to the interaction of the amino-terminal end of the fusion protein with the target cell membrane, is not a mechanism unique to HIV. It is made possible due to the presence, in oligomeric form, of the transmembrane glycoproteins of the virus. Bridging using chemical agents has made it possible to demonstrate trimers within the glycoproteins of the MuLV (Pinter et al., J. Virol., 30, 157–165, 1979), and MuMTV (Racevskis et al., J. Virol., 35, 937–948, 1980) envelope. It has also been shown that the RSV envelope protein forms oligomers which are found in infected cells and viral particles (Einfeld et al., Proc. Natl. Acad. Sci. USA, 85, 8688–8692, 1988). The influenza virus also expresses, at its surface, a haemagglutinin in trimeric form. In the latter case, the multimeric form is required for the intracellular transport of the protein (Copeland et al., J. Cell. Biol., 103, 1179–1191, 1986). The [lacuna] influenza also expresses, at its surface, a neuraminidase in the form of a tetramer (Varghese et al., Nature, 303, 35–40, 1983).

Although there is no doubt about the oligomeric nature of the various proteins encoded by the env gene, the monomer number has, itself, remained a controversial subject for a long time. The gp160 glycoprotein has, in fact, for a long time been described as being able to assemble into dimers or tetramers (Pinter et al., J. Virol., 63, 2674–2679, 1989; WO 94/00557 of the CNRS; Schawaller et al., Virology, 172, 367–369, 1989; Earl et al., Proc. Natl. Acad. Sci., 87, 648–652, 1990; Earl et al., J. Virology, 68, 3015–3026, 1994). Other more recent reports have, however, demonstrated that gp160 might, in fact, associate naturally, via its gp41 portion, in the form of trimers (Min Lu et al., Nature Structural Biology, 2, 1075–1082, 1995; Weisshorn et al., EMBO J., 15, 1507–1514, 1996; Weisshorn et al., Nature, 387, 426–430, 1997), the dimeric or tetrameric forms resulting, in fact, from aberrant interchain disulphide bridges or from transient oligomeric forms (see below).

For vaccinal purposes, the HIV envelope glycoprotein can be produced and purified, either by culturing the HIV virus on cell lines and purifying the glycoprotein from the culture medium (WO 94/00557 of the CNRS), or by expressing a recombinant of this protein using a vector other than HIV and purifying it from the culture medium (WO 91/13906, Chiron).

The purification of gp160 from cells infected with HIV makes it possible to obtain only tetramers, which is probably a transient oligomeric form, i.e. a form which does not correspond to that taken by its gp41 portion at the surface of the virus (WO 94/00557 of the CNRS).

The expression of a gp160 recombinant using a vector other than HIV, although having the advantage of escaping the dangers linked to the HIV infectious agent, does not make it possible also to have the "native" oligomeric structure of gp160. Specifically, VanCott et al. have shown that the recombinant gp160 expressed by vaccinia, although having the power to adhere to CD4, comprises structural differences (J. Imm. Meth., 183, p. 114, col. 1, li. 19–22, 1995). Randall et al. have also shown that the recombinant gp160 expressed by vaccinia comprises aberrant interchain disulphide bridges (Virology, 179, 827–833, 1990).

Recently, Parren et al. have demonstrated a correlation between the production of antibodies which can neutralize, in vitro, HIV infection of cells and the oligomeric nature of gp120 (J. of Virology, 72, 3512–3519, 1998). For this, Parren et al. used a gp120 expressed by HIV in infected cells, probably in order to get round the problems linked to the structural differences between a native gp120, expressed at the surface of HIV, and those produced by expression vectors such as vaccinia.

Moreover, it is known that antibodies specific for the oligomeric structure of gp160 can be generated (Earl et al., above), and participate, in fact, in a neutralizing effect against HIV infection of cells, in vitro.

The present invention is directed towards providing a method for obtaining recombinant env gene expression products, which allows the restoration of their trimeric form, this form possibly being used in the context of a vaccination or in carrying out a diagnosis of HIV infection. In fact, the clinical trials carried out on recombinant gp160 molecules pose the problem of the spectrum of inhibition, which remains limited to only a few viral strains (Pialoux et al., Aids Res. Hum. Retr., 11, 373–381, 1995; Salmon-Céron et al., Aids Res. Hum. Retr., 12, 1479–1486, 1995).

To date, although the trimeric form of a gp160 has been identified several times in a mixture of other polymeric forms, no-one has purified, nor suggested purifying, the trimeric form of gp160. The present [lacuna] is aimed at overcoming this need.

SUMMARY OF THE INVENTION

For this purpose, the invention relates to any purified recombinant glycoprotein which satisfies the following properties:

a) a capacity for adhesion to CD4;

b) an affinity with an anti-gp120 antibody capable of neutralizing HIV infection of cells, in vitro;

c) an affinity with an anti-gp41 antibody;

d) a trimeric form lacking interchain disulphide bridges.

A second subject of the present invention relates to a vaccine comprising the purified glycoprotein according to the invention, and an adjuvant.

A third subject of the present invention relates to the use of the glycoprotein according to the invention in the implementation of any method for diagnosing, in vitro, infections caused by HIV.

A final subject of the present invention relates to a method for obtaining a glycoprotein according to the invention, in which, by means of genetic recombination techniques, a glycoprotein satisfying the properties a), b) and c) according to the invention is expressed, purified and subjected to steps involving at least one reducing agent, one ionic detergent and/or one neutral detergent, under conditions such that a glycoprotein satisfying the conditions according to the invention is obtained.

BRIEF DESCRIPTION OF THE FIGURE

The figure represents the SDS PAGE analysis under reducing conditions obtained with a recombinantly produced gp160 that was purified and treated to make trimers (lanes 3–4) compared to gp160 dimers (lane 2), monomers (lane 5 and 6), and combination of dimmers, trimers, and tetramers (lane 7).

DETAILED DESCRIPTION OF THE INVENTION

Figure 1:
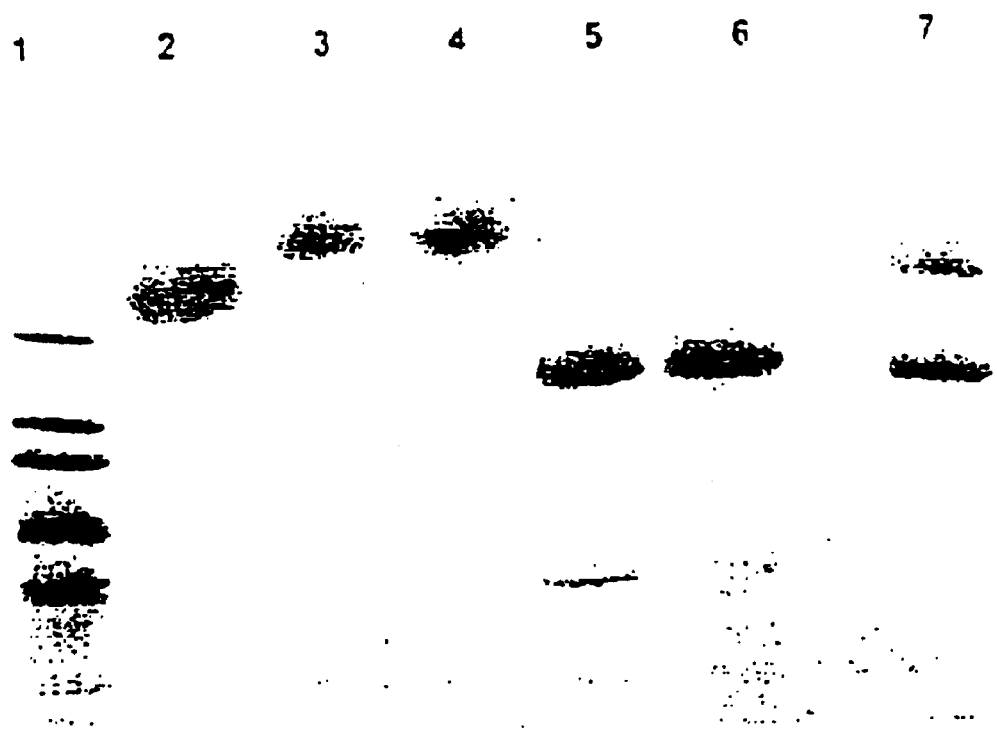

In the context of the present invention, the capacity for adhesion to CD4 can be determined by radio-immune precipitation, by ELISA or by surface plasmon resonance, the detail of these methods being set out in the remainder of the description. These methods can be modified within the limit of current knowledge, the objective being to simply make sure that the glycoprotein according to the invention indeed forms a complex with CD4.

The CD4 molecules can be prepared in all kinds of different ways, including purification from a natural source or using genetic recombination techniques. In this context, it is possible to use the CD4 molecules described in WO 89/03222, WO 89/02922, Smith et al. (Science, 238, 1704–1707, 1987) and Littman et al. (Nature, 325, 453–455, 1987), for example. The company ERC BioServices Corporation, 649A Lofstrand Lane, Rockeville, Md. 20850, USA, also sells a CD4 produced by CHO ST4.2 cells (In: Aids Research and Reference Reagent Program Catalog, the Nat. Inst. Health U.S.D.H.H.S.), for example.

Preferably, the capacity for adhesion is at least identical to that of a gp120 of an infectious HIV strain, for example a gp120 originating from the SF2, HXB2, BRU, MN, SC, NY5, CDC4, WMJ2, RF, MAL, ELI, Z96, Z3, Z321 and JY1 5 isolates (Myers et al., Human Retroviruses and Aids, Los Alamos, N.Mex., 1990), or from the other isolates described by Tersmette et al. (J. Virol., 62, 2026–2032, 1988), Popovic et al. (Science, 224, 497–500, 1984), and EP541753 (Transgene S.A.), for example.

The affinity ($K_d$) measured by surface plasmon resonance can also be of the order of $10^{-4}$ to $10^{-12}$ M, preferably $10^{-9}$ to $10^{-11}$ M, which is in accordance with the affinities already measured for gp120 molecules (Smith et al., Science, 238: 1704, 1987; Lasky et al., Cell, 50: 975, 1987), for example.

The recombinant glycoprotein according to the invention also has an affinity with an anti-gp120 antibody capable of neutralizing, in vitro, HIV infection of cells. The term "antibodies" includes all immunoglobulins or fragments of these immunoglobulins, of polyclonal, monoclonal or chimeric original [sic] (see U.S. Pat. No. 4,816,397), for example. All known antibodies, or antibodies likely to be prepared, capable of recognizing an epitope of gp120 and of neutralizing, in vitro, the infection of cells by an HIV may be taken into account in the context of the present invention. In order for an HIV glycoprotein to be considered as satisfying the needs of the present invention, it merely needs to have an affinity with an antibody of this type. Without wishing to be limited by the techniques and antibodies which can be used for the needs of the invention, mention may be made, by way of information, of the articles by VanCott et al. (1995, above) and Earl et al. (1994, above), for example.

With regard to the assays for measuring the neutralizing efficiency of an antibody in vitro, mention may be made of the articles by Pialoux et al. (1995, above) and Salmon-Céron et al. (1995, above), for example. In order to consider that the antibody satisfies the needs of the present invention, neutralization, in vitro, of HIV infection of cells merely has to be observed, whatever the neutralization threshold.

Moreover, the recombinant glycoprotein according to the invention also has an affinity with an anti-gp41 antibody. The comments set out above apply mutatis mutandis to gp41, with the difference that the neutralizing effect of an anti-gp41 antibody is not important, while at the same time possibly being a preferential criterion not to be ignored.

The measurement of the affinity of the glycoprotein in trimeric form with the anti-gp41 and anti-gp120 antibodies can be carried out through direct immunological reaction with the antibody, or by ELISA, for example. The operating conditions can vary within the limits of current knowledge, the variations and/or adaptations with respect to known techniques not, in fact, representing a difficult obstacle for those skilled in the art.

The trimeric form of the glycoprotein according to the invention can be observed on SDS PAGE gel, possibly under reducing conditions (see Example 1). Those skilled in the art may, however, use any kind of other analyses, such as analytical centrifugation or analysis by light diffusion. The objective is simply to demonstrate the association of three gp160 molecules which are not linked by interchain bridges.

The glycoprotein according to the invention, in satisfying the properties set out above, can therefore be composed of all or part of the gp41 protein, and of all or part of the gp120 protein. As a result, this glycoprotein can be encoded by all or part of an env gene, which may or may not be native (originating from an HIV isolate), said glycoprotein being either purified at a stage when the cleavage has not yet taken place in situ, or said cleavage being made nonfunctional either because of the nature of the cellular host, which does not have the required enzymes, because of inhibitors of these enzymes, or because the cleavage site has been genetically modified, for example.

The genetic modification of the cleavage site is well known to those skilled in the art, and makes it possible to obtain whole proteins, of varying sizes, containing all or part of the gp41 and all or part of the gp41 [sic]. By way of nonlimiting information, mention may be made of the gp160 and gp140 glycoproteins described by EP541753 (above), EP679187 (above), Earl et al. (1994, above) and Kieny et al. (1988, above), the technical teaching of this literature being incorporated by way of reference into the description of the present invention.

More particularly, it is possible to use, as a source of env gene, all known HIV isolates, in particular those described above. The cloning can be advantageously carried out by the PCR technique, followed by insertion of the DNA fragment into a suitable vector. The cleavage site(s) can then be deleted by site-directed mutagenesis, as described by Kieny et al. (1988, above) or in Example 1 below. The preparation of the vectors, and all the other technical procedures, can be carried out according to the protocols described in the manuals by Sambrook et al. (Molecular Cloning, A Laboratory Manual, Cold Spring Harbor Laboratory Press, U.S.A., 1989).

The expression vector in which the DNA fragment encoding a glycoprotein according to the invention is finally cloned can be a plasmid, a phage, a whole virus DNA, a cosmid, a DNA intended to integrate into a cell, etc. This vector preferably comprises sequences which regulate the expression of the env gene and, where appropriate, other sequences which regulate the translocation of the glycoprotein towards the membrane of the host producer cell. Host cells which are the most suitable, due to glycosylation which is close, or even identical, to that desired, are higher eukaryotic cells, which can include, for example, immortalized cell lines originating from monkeys (Cos-7, ATCC CRL 1651; Vero76, ATCC CRL 1587), from hamsters (BHK, ATCC CRL 10; CHO, PNAS USA, 77: 4216, 1980), from mice (TM4, Mather, Biol. Reprod., 23, 243–251, 1980), from humans (Hela, ATTC CCL2; W138, ATCC CCL75; Hep G2; HB 8065), or from dogs (MDCK, ATCC CCL34), etc.

The most suitable expression vectors are those which reproduce in eukaryotes, in particular the vaccinia virus which is well known in the prior art (WO 86/07593), for example.

In a particular embodiment of the present invention, it is possible to produce in particular gp160 molecules according to the teaching described in EP541753 (above), or gp140 molecules according to the method of Earl et al., (1990, above), or even any other glycoprotein variant in which one or more portions of gp41and/or gp120 will be removed, the objective being that the, gp41 portion is sufficient for trimer formation to take place, and that the gp120 portion is sufficient to be recognized by neutralizing anti-gp120 antibodies and by CD4. In order to choose modified env genes which satisfy the needs of the present invention, those skilled in the art are able to proceed step by step or randomly, and then to choose, from the sequences which do not satisfy our needs, those which do satisfy them.

After having produced the glycoprotein by genetic recombination techniques or by HIV infection of cells, it is purified by means of techniques known to those skilled in the art, in particular those which involve lentil lectins (Pialoux et al., 1995, above; Salmon-Céron et al., 1995, above), those described in WO 91/13906 (above) which can also be optionally adapted to the needs of the present invention, or even those described in Example 1 (immunoaffinity), for example.

With regards to the recombinant proteins, it may be noted that a portion of the glycoproteins thus purified has interchain disulphide bridges, whatever the nature of the host or of the vector used. The glycoproteins associate, in fact, as dimers (a portion being covalent) which are visible on SDS PAGE gel after fixing with a bridging agent. With regards to the glycoproteins purified from HIV infected cells, they are also in the form of tetramers (WO 94/00557, above).

In order to satisfy the needs of the present invention, the glycoproteins are therefore dissociated, and then they are subjected to conditions which promote their natural reassembly, i.e. in the form of trimers. For this, the glycoprotein is subjected to steps which involve at least one reducing agent, one ionic detergent and/or one neutral detergent, under conditions such that a glycoprotein which satisfies the needs of the present invention is obtained.

One or more reducing agent(s) may be chosen from dithiothreitol, β-mercaptoethanol, reduced glutathione or sodium borohydride molecules, for example.

One or more ionic detergent(s) may be chosen from the salts of dodecyl sulphate, in particular sodium dodecyl sulphate (SDS) or lithium dodecyl sulphate, the salts of dioctyl sulphosuccinate (sodium dioctyl sulphosuccinate, for example), the salts of cetyltrimethylammonium (bromium cetyltrimethylammonium, for example), the salts of cetylpyridinium (chlorine cetylpyridinium, for example), the N-dodecyl- or N-tetradecylsulphobetaines, the zwittergents 3-14 and 3-[(3-chlolamidopropyl)dimethylamino]-1-propane sulphonate (CHAPS), for example.

Similarly, one or more neutral detergent(s) may be chosen from tween20®, tween80®, octylglucoside, laurylmaltoside, hecameg®, lauryldimethylamine, decanoyl-N-methylglucamide, polyethylene glycol lauryl ether, triton X100® and Lubrol PX®, for example.

The operating conditions should be sufficient to dissociate the glycoproteins and reassemble them as trimers. For this, generally, the glycoproteins can be dissociated using one or more ionic detergent(s), in the presence or absence of a reducing agent, and then the reassembly of the monomers can be promoted by substituting the ionic detergent with a neutral detergent, by means of dialysis, for example. In this way, the production of a glycoprotein according to the invention, comprising less than 50% of other protein contaminants (mainly consisting of covalent dimers), is ensured.

Preferably, in order to obtain exclusively glycoprotein trimers according to the invention, the purified glycoproteins are subjected, in the course of the treatment, to a reducing agent so as to release the covalent dimers, free sulphydryl functions are, where appropriate, blocked by means of suitable molecules, for instance alkylating agents such as N-ethylmaleimide or iodoacetamide, and then the remaining sulphydryl functions are gently reoxidized in the presence of an oxidizing agent such as oxidized glutathione, for example.

In a particular embodiment of the present invention, the purified glycoprotein can be subjected successively to a reducing agent, to an alkylating agent, to an oxidizing agent, to an ionic detergent and to dialysis against a neutral detergent, for example.

In another particular embodiment of the present invention, the purified glycoprotein can be subjected successively to an ionic detergent, to a reducing agent, to an oxidizing agent and to dialysis against a neutral detergent.

At the end of the method the neutral detergent can be substituted with a suitable buffer, for example by means of dialysis.

Another subject of the present invention relates to a vaccine comprising the glycoprotein according to the present invention, and an adjuvant. This vaccine can contain, as an HIV surface antigen, only the glycoprotein according to the present invention, the dimeric or monomeric forms of a gp160 or gp120 being specifically excluded, for example, for reasons of reduced immunogenicities. Other valences concerning other diseases can also be added to this vaccine, the amounts of antigens and/or the formulation of each valence probably having, however, to be optimized so as to ensure an effective immune response, for example. The valences of other pathogens can originate from bacteria, from viruses or from parasites, for example those causing hepatitis (types A to G), measles, mumps, polio, tuberculosis, diphtheria, malaria, etc.

Among the adjuvants which can be used, it is possible to list all the aluminium salts, such as the aluminium phosphates and hydroxides; Freund's adjuvant; N-acetylmuramyl-L-alanyl-D-isoglutamyl-L-alanine-2-[1, 2-dipalmitoyl-sn-glycero-3-(hydroxyphosphoryloxy)] (see Sanchez-Pescador et al., J. Immu., 141, 1720–1727, 1988); the molecules derived from *Quillaja saponaria*, such as Stimulon® (Aquila, US); the Iscoms® (CSL Ltd, US); all molecules based on cholesterol and analogues, such as DC Chol® (Targeted Genetics); the glycolipid Bay R1005® (Bayers, Del.); the antigens of *Leishmania brasiliensis*, such as LeIF (technical name) available from Corixa Corp. (US), the polymers of the polyphosphazene family, such as Adjumer (technical name) available from the "Virus Research Institute" (US).

The vaccine compositions according to the invention can be used for preventing HIV-1 infections, the dose and the route and frequency of administration probably having, however, to be optimized so as to obtain an effective immune response.

A final subject of the present invention relates to the use of the glycoprotein according to the invention in the implementation of any method for diagnosing, in vitro, infections caused by HIV.

Other characteristics of the present invention will become apparent in the course of the following descriptions of examples of embodiments, which are provided for the purposes of illustrating the present invention and which are not intended to be limiting. The manipulation of the cells, the preparation of the vectors, the transformation of cells and all the other technical procedures are, where not otherwise specified, carried out according to the protocols described in the manual by Sambrook et al. (1989, above). These examples are preceded by a brief description of FIG. 1 and of the methods measuring the affinity of gp160 for CD4.

Demonstration of an affinity for CD4 by radio-immune precipitation: a recombinant CD4 labelled with sulphur 35, produced by CHO cells (Genentech, USA; VanCott et al., 1995, above), is used. Coprecipitation experiments are then carried out, during which the CD4 is added, in an increasing amount, to a fixed amount of purified gp160 in trimeric form in order to determine the saturation point, and then they are coprecipitated with an anti-gp160 antiserum. For this, the CD4 and the gp160 are mixed for 1 h at 4° C., the antibody (OKT4, Ortho Diagnostics, US) antibody is added, and the complexes are washed and separated by electrophoresis.

Demonstration of an affinity for CD4 by ELISA: the measurement of the affinity constants of CD4 for the glycoprotein according to the invention is carried out using the technique of Friguet et al. (J. of immunological methods, 77, 305–319, 1985).

Measurement of the affinity of the gp120 on CD4 by surface plasmon resonance: the Biacore® is a machine for analysing biospecific interactions in real time and without labelling, which uses the principle of surface plasmon resonance. During the analysis, one of the interacting components (the ligand) is coupled to a hydrophilic (dextran) or hydrophobic (HPA surface) matrix. The other interacting component (analyte) passes in contact with the surface via a microfluid transfer cartridge. The increase in mass close to the surface due to the interaction between the molecules is represented as a function of time on a sensorgram. Various types of coupling chemistry allow for the attachment of practically all the biomolecules to the matrix. The user therefore creates a biospecific surface which is tailor-made for each type of application. In practice, the glycoprotein according to the invention is coupled to the matrix and various concentrations of CD4 are sent, by the machine, into contact with this matrix. Each time, the mass of CD4 attached to the glycoprotein is recorded. The Biaeval3® software automatically calculates the dissociation constant of the CD4 on the gp120.

FIG. 1: representation of the SDS PAGE analysis under reducing conditions, obtained with the gp160 produced by VVTG9150, purified, treated to make trimers and attached using a bridging agent (col. 3 and 4); in comparison with that obtained under reducing conditions with the gp160 produced by VVTG9150, purified and directly attached (col. 2); in comparison with that obtained under reducing conditions with monomers of gp160 (col. 5 and 6); and in comparison with that obtained under nonreducing conditions with the gp160 produced by VVTG9150 and purified (col. 7).

EXAMPLE 1

A recombinant vector based on the vaccinia virus, VVTG9150, is used for the production of gp160. The construction of the plasmid for transferring the gene encoding the hybrid env protein HIV-1$_{MN/LAI}$ into the genome of, the vaccinia virus VVTG9150 is described below.

The PstI-KpnI DNA fragment of pTG1163, ref. Kieny et al. (Prot. Eng., 2, 219–225, 1998), which contains the sequence encoding the signal peptide and the first amino acids of the gp120 of the HIV-1$_{LAI}$ virus, is inserted at the PstI and KpnI sites of the bacteriophage M13TG130, ref. Kieny et al. (Gene, 26, 91–99, 1983), generating M13TG4147. The PstI—PstI fragment of pTG1163, containing all of the gene encoding a gp160/soluble of HIV-1$_{LAI}$, is introduced into the PstI restriction site of M13mp70, generating M13TG4137. The DNA of the bacteriophage M13TG4137 is then cleaved with BglII, digested with polymerase I (Klenow fragment) in order to generate a blunt end, and then cleaved with EcoRI, in order to be inserted at the EcoRV and EcoRI sites of the bacteriophage M13TG4147, generating M13TG4158. A deletion is then produced on M13TG4158, with an oligonucleotide, which allows the introduction of an SphI site and of an SmaI site. The bacteriophage M13TG4168 is obtained. The gene encoding gp120 is then amplified from DNA of SupT1 cells infected with the HIV-1$_{MN}$ virus, by the PCR technique with oligonucleotides which introduce SphI and SmaI sites, respectively. The amplified DNA fragment is then digested with SphI and SmaI and inserted at the corresponding sites of M13TG4168, generating M13TG4174. Site-directed mutagenesis is carried out on M13TG4174 with an oligonucleotide which makes it possible to mutate a potential transcription stop site (TTTTTNT) recognized by the vaccinia virus in the early genes, and to introduce an EcoRI restriction site, thus generating M13TG8120. The PstI—PstI fragment of M13TG8120 is then cloned into the PstI site of the plasmid pTG9148, generating pTG9150 (the virus VVTG9150 after transfection).

pG9148 is, moreover, generated in the same way: the sequence corresponding to the H5R promoter of the vaccinia virus is amplified by the PCR technique with oligonucleotides which introduce BamHI and BglII sites, respectively. The amplified DNA fragment is then digested with BglII and BamHI and inserted at the corresponding sites of M13TG6131 (Gene, 26, 91–99, 1983), generating M13TG8124. The BamHI-BglII fragment of M13TG8124 containing the H5R promoter sequence is introduced into the BamHI restriction site of pTG9133, generating pTG9145. The plasmid pTG9133 was constructed by introducing a BamHI site between the ClaI and EcoRI sites of pTG1H-TK (Nature, 312, 5990, 163–166, 8 Nov. 1984), by ligating an OTG4451/OTG4452 linker. A multiple cloning site derived from M13TG131 digested with BglII and EcoRI is introduced into the BamHI and EcoRI sites of pTG9145, generating pTG9148.

In conclusion, VVTG9150 therefore encodes a hybrid and soluble gp160 in which the gp120 portion derives from HIV-1MN, and the gp41 transmembrane portion originates from an LA1 isolate. Several modifications are also introduced into this coding sequence. Firstly, an SphI restriction site is created immediately downstream of the sequence encoding the signal peptide, without modifying the amino acid sequence. Secondly, a SmaI restriction site is created immediately above the cleavage sequence between the gp120 and the gp41, without modifying the amino acid sequence. Thirdly, the two cleavage sites at position 507–516 (amino acid numbering in accordance with Myers et al., in: Human retroviruses and AIDS, Los Alamos Nat. Lab., USA, 1994) are mutated (original sequence KRR . . . REKR mutated to QNH . . . QEHN). Fourthly, the sequence encoding the hydrophobic transmembrane peptide IFIMIVGGLVGLRIVFAVLSIV (amino acids 689–710 of Myers et al.) is deleted. Fifthly, a stop codon has been substituted for the second E codon encoding PEGIEE (amino acids 735–740 of Myers et al.), i.e. the $29^{th}$ amino acid of the intracytoplasmic domain.

VVTG9150 is then propagated in order to produce the hybrid gp160 on BHK21 cells, under conventional conditions (Nature, 312, 163–166, 1984).

The hybrid gp160 glycoprotein is then purified successively by ion exchange chromatographies, immunoaffinity chromatography, gel filtration, and concentration. In summary, the culture medium containing the gp160 is passed successively through two DEAE Trisacryl LS Plus® supports, equilibrated in BPG200® and BPG100® columns (Pharmacia) with a pH 8.3 buffer containing 2.42 g/l of Tris and 1 ml/l of triton X100. Then, the elution fractions containing the gp160 are passed through an AF-Tresyl Toyopearl® (Tosoh Corp, JP) onto which the antibody IAM5F3 has been grafted and which has been equilibrated in a buffer composed of 29.22 g/l of NaCl, 2.42 g/l of Tris and 1 ml/l of triton X100. The elution is collected as soon as the increase in OD is seen on the display, this collection being until return to base line. The pH of the elution is then neutralized with 4% (v:v) of 2M Tris HCl buffer. The neutralized elution is subjected to gel filtration in an XK 50/100® column containing the sephacryl HR S300 support equilibrated in a PBS buffer. If the protein concentration is then lower than 0.44 mg/ml, the elution is concentrated in an Amicon® cell equipped with a YM30 membrane. Then, the elution or the concentrate is inactivated in a water bath at 60° C. for 1 h, and it is filtered (0.22 $\mu$m) in a Nalgene® flask. It is thus possible to obtain approximately 1.34 mg/ml of gp160 which is 91% pure (visualized on SDS PAGE).

Starting with 560 $\mu$l of purified gp160 (1 mg/ml), 65 $\mu$l of 1M sodium phosphate buffer, pH 7.8; 5.5 $\mu$l of distilled water and 19.5 $\mu$l of 250 mM dithiothreitol (DTT) are added, and the mixture is vortexed for 15 s. 51.5 $\mu$l of 1M sodium phosphate ($NaH_2PO_4$), are added, then the sulphydryl groups are blocked by adding 95 $\mu$l of 100 mM N-ethylmaleimide, the mixture is incubated for 15 min, the sulphydryl groups are reoxidized by adding 32.5 $\mu$l of reduced glutathione at 150 mM and 484 $\mu$l of oxidized glutathione at 100 mM, and the mixture is incubated for 30 min. The gp160 dimers are then dissociated by adding 13.2 $\mu$l of sodium dodecyl sulphate (SDS) at 10%. The sample is placed in a dialysis cassette with a volume of 3 ml, against 3 l of PBS buffer with 10 mM of octylglucoside. The dialysis is carried out overnight at room temperature with gentle stirring. The detergent is finally eliminated by one or more new dialyses against PBS buffer. The gp160 molecules thus treated are exclusively in the form of trimers.

FIG. 1 represents the SDS PAGE analysis under reducing conditions (DTT), obtained with the gp160 produced by VVTG9150, purified, treated to make trimers and attached using the bifunctional bridging agent ethylene glycol-bis (succinimidyl succinate) (EGS) (col. 3 and 4); in comparison with that obtained under reducing conditions with the gp160 produced by VVTG9150, purified and directly attached using the EGS (col. 2: dimers); and in comparison with that obtained under reducing conditions with monomers of gp160 (col. 5 and 6); and in comparison with that obtained under nonreducing conditions with the gp160 produced by VVTG9150 and purified (col. 7: in the absence of a reducing agent, the interchain linkages lead to the formation of dimers, trimers and tetramers).

EXAMPLE 2

Using the vaccinia virus, a gp120 which is extended by the first 129 amino acids of the N-terminal portion of gp41, as described by Earl et al., Proc. Natl. Acad. Sci. USA, 87, 648–652, 1990, is expressed. In so far as the gp41 portion is limited to its first 129 amino acids, it does not comprise a transmembrane region. This glycoprotein exhibits, on SDS PAGE gel, a molecular weight of the order of 140 kD and is commonly termed gp140.

This gp140 is purified successively by ion exchange chromatography, affinity chromatography with lentil lectins, and by gel filtration, as described by Pialoux et al. (1995, above) and Salmon-Céron et al. (1995, above)

Starting with 100 $\mu$l of purified gp140 (1 mg/ml), 2 $\mu$l of 250 mM dithiothreitol (DTT) and 10 $\mu$l of SDS (10%) are added, the mixture is incubated for 15 min, 20 $\mu$l of oxidized glutathione (250 mM) are added to it, it is incubated overnight at 4° C., and then the sample is placed in a dialysis cassette with a volume of 3 ml, against 3 l of PBS buffer containing 10 mM of octylglucoside. The dialysis is carried out overnight at room temperature with gentle stirring. The detergent is finally eliminated by one or more new dialyses against PBS buffer. Against all expectations, this method makes it possible to eliminate all the interchain disulphide bridges without it being necessary to block the sulphydryl groups with an alkylating agent. The gp140 molecules thus treated are exclusively in the form of trimers.

EXAMPLE 3

Using the vaccinia virus, a gp160 as described by Kieny et al. (Protein Engineering, 2, 219–225, 1988) is expressed. It is purified as described in Example 1 and then treated with SDS, and it is dialysed against a PBS buffer containing 10 mM of octylglucoside. After treatment, a mixture of non-covalent trimers and of covalent dimers of the gp160 is obtained, the predominant form consisting of trimers.

What is claimed is:

1. A composition comprising a purified recombinant trimer of HIV gp160 wherein the trimer:

a) binds to CD4;

b) binds to an anti-gp120 antibody capable of neutralizing HIV infection of cells in vitro;

c) binds to an anti-gp41 antibody; and d) has no inter-chain disulfide bridges.

2. The composition according to claim 1, wherein the gp160 comprises a gp41 and a gp120 form different HIV strains.

3. A composition comprising a purified recombinant trimer of HIV gp160 wherein all or a portion of the gp160 transmembrane region is deleted, and were the trimer:

a) binds to CD4;

b) binds to an anti-gp120 antibody capable of neutralizing HIV infection of cells in vitro;

c) binds to an anti-gp41 antibody; and d) has no inter-chain disulfide bridges.

4. The composition according to any one of claims 1–3 having a protein content that comprises more than 50% of the trimer.

5. The composition according to any one of claims 1–3 wherein the binding affinity of the trimmer to CD4 is equal or greater than the binding affinity of gp120 of and infectious HIV.

6. The composition of any one of claims 1–3 further comprising an adjuvant.

7. The composition according to claim 6 wherein the trimer is the only HIV surface antigen in the composition.

8. A method of producing the trimer according to any one of claims 1–2, the method comprising, in order:

a) expressing gp160;

b) purifying the gp160;

c) contacting the gp160 with a reducing agent;

d) contacting the gp160 with an alkylating agent;

e) contacting the gp160 with an oxidizing agent;

f) contacting the gp160 with an ionic detergent, and g) dialyzing the gp160 with a neutral detergent.

9. A method of producing the trimer according to any one of claims 1–2, the method comprising, in order:

a) expressing gp160;

a) purifying the gp160;

b) contacting the gp160 with an ionic detergent;

c) contacting the gp160 with a reducing agent;

d) contacting the gp160 with an oxidizing agent; and e) dialyzing the gp160 against a neutral detergent.

10. A method of producing the trimer according to claim 3, the method comprising, in order:

a) expressing gp160 having its transmembrane region deleted therefrom;

b) purifying the gp160;

c) contacting the gp160 with a reducing agent;

d) contacting the gp160 with an alkylating agent;

e) contacting the gp160 with an oxidizing agent;

f) contacting the gp160 with an ionic detergent, and g) dialyzing the gp160 with a neutral detergent.

11. A method of producing the trimer according to claim 3, the method comprising, in order:

a) expressing gp160 having its transmembrane region deleted therefrom;

b) purifying the gp160;

c) contacting the gp160 with an ionic detergent;

d) contacting the gp160 with a reducing agent;

e) contacting the gp160 with an oxidizing agent; and f) dialyzing the gp160 against a neutral detergent.

12. A composition comprising a purified recombinant trimer of HIV pg160 comprising a gp41 fragment essential for trimer formation and an immunogenic fragment of gp120, wherein the trimer:

a) binds to CD4;

b) binds to an anti-gp120 antibody capable of neutralizing HIV infection of cells in vitro;

c) binds to an anti-gp41 antibody; and d) has no inter-chain disulfide bridges.

13. The composition according to claim 12, wherein the gp41 and gp120 are from different HIV strains.

14. The composition according to any one of claims 12–13 having a protein content that comprises more than 50% of the trimer.

15. The composition according to any one of claims 12–13 wherein the binding affinity of the trimer to CD4 is equal or greater than the binding affinity of gp120 of an infectious HIV.

16. The composition of any one of claims 12–13 further comprising an adjuvant.

17. The composition according to claim 16, wherein the trimer is the only HIV surface antigen in the composition.

18. A method of producing the trimer according to any one of claims 12–13, the method comprising, in order:

a) expressing a gp160 fragment comprising gp41 and an immunogenic gp120 fragment;

b) purifying the gp160 fragment;

c) contacting the gp160 fragment with a reducing agent;

d) contacting the gp160 fragment with an alkylating agent;

e) contacting the gp160 fragment with an oxidizing agent;

f) contacting the gp160 fragment with an ionic detergent, and g) dialyzing the gp160 fragment with a neutral detergent.

19. A method of producing the trimer according to any one of claims 12, 13, the method comprising, in order:

a) expressing a gp160 fragment comprising gp41 and an immunogenic gp120 fragment;

b) purifying the gp160 fragment;

c) contacting the gp160 fragment with an ionic detergent;

d) contacting the gp160 fragment with a reducing agent;

e) contacting the gp160 fragment with an oxidizing agent; and f) dialying the gp160 fragment against a with neutral detergent.

20. The composition according to claim 12 wherein the gp41 fragment essential for trimer formation comprises gp41 lacking its transmembrane domain.

21. The composition according to claim 20 wherein the gp41 fragment comprises the 129 N-terminal amino acids of gp41.

* * * * *

UNITED STATES PATENT AND TRADEMARK OFFICE
CERTIFICATE OF CORRECTION

PATENT NO.    : 6,737,067 B1
DATED         : May 18, 2004
INVENTOR(S)   : Michel Chevalier It is certified that error appears in the above-identified patent and that said Letters Patent is hereby corrected as shown below:

Column 1,
Line 5, please replace "file Jul. 29, 1999." with -- filed Jul. 29, 1999 --.

Column 3,
Line 29, please replace "dimmers" with -- dimers --.

Column 5,
Line 42, please delete "," following "the".

Column 6,
Line 20, please replace "3-[(3chloamidopropyl)dimethylamino]-1-propane" with
-- 3-[(3cholamidopropyl)dimethylamino]-1-propane --.

Column 8,
Line 27, please delete "," following "of".
Line 47, please replace "gp120" with -- $gp120_{MN}$ --.

Column 11,
Line 4, please replace "form" with -- from --.
Line 8, please replace "were" with -- wherein --.
Line 19, please replace "trimmer" with -- trimer --.
Line 20, please replace "and" with -- an --.
Line 35, please replace "g) dialyzing the gp160 with a neutral detergent" with -- g) dialyzing the gp160 against a neutral detergent --.

Column 12,
Line 43, please replace "claims 12, 13" with -- claims 12-13 --.

Signed and Sealed this

Twenty-first Day of December, 2004

JON W. DUDAS
*Director of the United States Patent and Trademark Office*